United States Patent
Erspamer et al.

(10) Patent No.: US 6,479,415 B1
(45) Date of Patent: *Nov. 12, 2002

(54) ABSORBENT STRUCTURES HAVING FLUID ACQUISITION AND DISTRIBUTION LAYER

(75) Inventors: John P. Erspamer, Barden, TN (US); S. K. Laurence Li, British Columbia (CA); Samuel Charles Baer, Germantown, TN (US)

(73) Assignee: BKI Holding Corporation, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/232,783

(22) Filed: Jan. 19, 1999

Related U.S. Application Data

(60) Provisional application No. 60/088,455, filed on Jun. 8, 1998, provisional application No. 60/088,456, filed on Jun. 8, 1998, and provisional application No. 60/102,344, filed on Sep. 29, 1998.

(51) Int. Cl.[7] ............................................. B32B 21/10
(52) U.S. Cl. ................... 442/381; 442/385; 442/389; 442/393; 442/416; 442/417
(58) Field of Search ............................... 442/381, 385, 442/389, 393, 416, 417

(56) References Cited

U.S. PATENT DOCUMENTS

| | | | |
|---|---|---|---|
| 3,993,616 A | 11/1976 | Gross .......................... 260/29.4 |
| 4,056,103 A | 11/1977 | Kaczmarzyk et al. ....... 128/285 |
| 4,084,033 A | 4/1978 | Drelich ........................ 428/198 |
| 4,117,184 A | 9/1978 | Erickson et al. ............. 428/224 |
| 4,364,992 A | 12/1982 | Ito et al. ....................... 428/23 |
| 4,410,571 A | 10/1983 | Korpman ................. 427/385.5 |
| 4,424,247 A | 1/1984 | Erickson .................... 428/138 |
| 4,444,830 A | 4/1984 | Erickson .................... 428/246 |
| RE31,822 E | 2/1985 | Erickson et al. ............ 128/156 |
| 4,529,739 A | 7/1985 | Scott et al. .................... 521/72 |
| 4,559,243 A | 12/1985 | Passler et al. .............. 427/209 |
| 4,578,068 A | 3/1986 | Kramer et al. .............. 604/368 |
| 4,645,789 A | 2/1987 | Dabi ........................... 524/379 |
| 4,649,164 A | 3/1987 | Scott et al. .................. 521/149 |
| 4,721,647 A | 1/1988 | Nakanishi et al. .......... 428/283 |
| 4,773,903 A | 9/1988 | Weisman et al. ........... 604/368 |
| 4,813,945 A | 3/1989 | Le-Khac .................... 604/367 |
| 4,892,533 A | 1/1990 | Le-Khac .................... 604/368 |
| 4,914,170 A | 4/1990 | Chang et al. ............... 526/240 |
| 5,057,166 A | 10/1991 | Young, Sr. et al. ......... 156/62.2 |
| 5,061,235 A | 10/1991 | Hogan ......................... 600/21 |
| 5,064,689 A | 11/1991 | Young, Sr. et al. .......... 427/202 |
| 5,100,397 A | 3/1992 | Poccia et al. ............... 604/365 |
| 5,135,792 A | 8/1992 | Hogan ......................... 428/74 |
| 5,176,670 A | 1/1993 | Roessler et al. ............. 604/378 |
| 5,188,624 A | 2/1993 | Young, Sr.et al. ........... 604/378 |
| 5,230,959 A | 7/1993 | Young, Sr. et al. ......... 428/372 |
| 5,268,419 A | 12/1993 | Stack et al. .................. 524/831 |
| 5,300,054 A * | 4/1994 | Feist et al. ................... 604/378 |
| 5,300,192 A | 4/1994 | Hansen et al. .............. 162/184 |
| 5,308,896 A | 5/1994 | Hansen et al. ................ 524/13 |
| 5,336,554 A | 8/1994 | Knight ........................ 428/230 |
| 5,338,766 A | 8/1994 | Phan et al. .................... 521/63 |
| 5,352,480 A | 10/1994 | Hansen et al. .............. 427/202 |
| 5,432,000 A | 7/1995 | Young, Sr. et al. ......... 428/372 |
| 5,439,458 A * | 8/1995 | Noel et al. .................. 604/378 |
| 5,447,977 A | 9/1995 | Hansen et al. ................ 524/13 |
| 5,498,478 A | 3/1996 | Hansen et al. .............. 428/372 |
| 5,516,585 A | 5/1996 | Young, Sr. et al. ......... 428/372 |
| 5,538,783 A | 7/1996 | Hansen et al. .............. 428/283 |
| 5,543,215 A | 8/1996 | Hansen et al. .............. 428/283 |
| 5,547,541 A | 8/1996 | Hansen et al. ................ 162/12 |
| 5,547,745 A | 8/1996 | Hansen et al. .............. 428/283 |
| 5,558,658 A | 9/1996 | Menard et al. ........... 604/385.1 |
| 5,571,618 A | 11/1996 | Hansen et al. .............. 428/359 |
| 5,589,256 A | 12/1996 | Hansen et al. .............. 428/283 |
| 5,591,149 A | 1/1997 | Cree et al. ................... 604/378 |
| 5,607,759 A | 3/1997 | Hansen et al. .............. 442/417 |
| 5,609,727 A | 3/1997 | Hansen et al. .............. 162/184 |
| 5,611,885 A | 3/1997 | Hansen et al. .............. 156/326 |
| 5,614,570 A | 3/1997 | Hansen et al. ................ 524/13 |
| 5,641,561 A | 6/1997 | Hansen et al. .............. 442/417 |
| 5,645,542 A | 7/1997 | Anjur et al. ................. 604/368 |
| 5,672,418 A | 9/1997 | Hansen et al. .............. 428/283 |
| 5,693,411 A | 12/1997 | Hansen et al. .............. 428/283 |
| 5,728,081 A * | 3/1998 | Baer et al. ................... 604/370 |
| 5,763,067 A | 6/1998 | Bruggemann et al. ... 428/317.9 |
| 5,789,326 A | 8/1998 | Hansen et al. ................ 442/59 |
| 5,800,419 A | 9/1998 | Soga et al. .................. 604/368 |
| 5,807,364 A | 9/1998 | Hansen et al. .............. 604/367 |
| 5,844,039 A | 12/1998 | Scranton et al. ............ 524/530 |
| 5,859,074 A | 1/1999 | Rezai et al. ................... 521/54 |
| 5,938,650 A | 8/1999 | Baer et al. ................... 604/368 |
| 5,944,706 A | 8/1999 | Palumbo et al. ............ 604/368 |
| 5,977,014 A | 11/1999 | Pilischke et al. ............ 502/401 |
| 5,998,312 A | 12/1999 | Kroesbergen ............... 442/221 |
| 6,013,954 A | 8/2000 | Grondin et al. ............. 604/370 |

FOREIGN PATENT DOCUMENTS

WO   WO 98/24621   6/1998   ............. B32B/5/26

* cited by examiner

Primary Examiner—Elizabeth M. Cole
(74) Attorney, Agent, or Firm—Darby & Darby

(57) ABSTRACT

Disclosed is an absorbent structure including a liquid acquisition layer and a fibrous liquid storage layer in liquid communication with the acquisition layer. The storage layer includes SAP particles. The acquisition layer includes synthetic fibers and the fibers are latex bonded. A fluid acquisition and/or distribution layer (ADL) containing at least two layers, a top layer of latex bonded synthetic fibers and a bottom layer of latex and/or thermal bonded cellulose fibers and method for preparation thereof are disclosed. The synthetic fiber layer is highly porous and provides rapid fluid acquisition under load. The cellulose layer provides z-direction capillary force to pull fluid into the absorbent product, to provide temporary fluid immobilization, and to act as a conduit for fluid to be pulled into unsaturated portion of the permanent fluid storage layer. The ADL of the invention provides increased protection against leakage relative to single-layer ADLS.

22 Claims, No Drawings

ABSORBENT STRUCTURES HAVING FLUID ACQUISITION AND DISTRIBUTION LAYER

This application claims priority under 35 USC §119 from U.S. Provisional Application Serial Nos. 60/088,455, 60/088,456 and 60/102,344 filed on Sep. 9, 1998 both of which are hereby incorporated herein by reference.

FIELD OF THE INVENTION

The present invention is directed to improved fibrous absorbent structures having separate layers for fluid acquisition, distribution, and storage. The acquisition layer contains latex-bonded synthetic fibers, and is useful in providing improved disposable absorbent products, such as diapers, adult incontinence pads, and sanitary napkins.

BACKGROUND OF THE INVENTION

Absorbent articles such as disposable diapers, adult incontinence pads, sanitary napkins, and the like, are generally provided with an absorbent core, or storage layer, to receive and retain bodily liquids. The absorbent core is usually sandwiched between a liquid pervious top sheet, whose function is to allow the passage of fluid to the core, and a liquid impervious backsheet which contains the fluid and prevents it from passing through the absorbent article. An absorbent core (e.g., for diapers and adult incontinence pads) typically includes fibrous batts or webs constructed of defiberized, loose, fluffed, hydrophilic, cellulosic fibers. The core may also include superabsorbent polymer (SAP) particles, granules, flakes or fibers. In addition, an absorbent article may contain a distribution layer that aids in transporting liquid quickly from the acquisition layer to the storage layer of the core.

In recent years, market demand for thinner and more comfortable absorbent articles has increased. Such articles may be obtained by decreasing the thickness of the diaper core, by reducing the amount of fibrous material used in the core while increasing the amount of SAP particles, and by calendering or compressing the core to reduce caliper and hence, increase density. However, higher density cores do not absorb liquid as rapidly as lower density cores because densification of the core results in smaller effective pore size. Accordingly, to maintain a suitable liquid absorption rate, it is necessary to provide a lower density layer having a larger pore size above the high density absorbent core to increase the rate of uptake of liquid discharged onto the absorbent article. The low density layer is typically referred to as an acquisition layer.

The storage layer portion of a disposable diaper core for example, is generally formed in place, during the converting process, from loose, fluffed cellulose. Superabsorbent powder is blended with the fluff cellulose fibers as the absorbent core is formed on the diaper converting line. Such cellulose material is generally not available in preformed roll form because it exhibits insufficient web strength, due to the lack of interfiber bonding or entanglement.

The acquisition layer portion of a disposable diaper is generally a carded synthetic staple fiber web that is thermally bonded, latex bonded, or point bonded. Typical staple fibers for acquisition layers are crimped polyester (PET) or polypropylene fibers that have a size of 6 to 15 denier and a length of at least 40 mm. The acquisition layer is formed, bonded and slit as a homogenous rolled good on a dedicated nonwoven textile production line. The slit roll of acquisition layer material is subsequently unrolled onto the diaper converting line where it is affixed on top of the absorbent core and below the topsheet. Examples of commercial infant diapers with a bonded carded staple fiber are Huggies Diapers produced by Kimberly-Clark Corp. (Dallas, Tex.) and private label diapers produced by Paragon Trade Brands (Atlanta, Ga.).

Modern infant disposable diaper converting machines have become extremely complex as more and more features such as elastication and multiple nonwovens have been implemented to improve diaper performance. This complexity has created significant raw material handling issues and a resultant loss of converting line productivity. There is a need to replace the bulky and cumbersome fluff pulp and superabsorbent powder forming systems with a single material that can simply be fed directly into the converting line from a roll or other suitable compact package. Because the acquisition layer and absorbent core are placed together in the final product, it can maximize the efficiency of the converting operation to combine the fluid acquisition layer and the absorbent core in a single material.

Ultra-thin feminine napkins are generally produced from roll-goods based nonwoven material. Such a roll of preformed absorbent core material is unwound directly onto the absorbent article converting equipment without the defiberization step required for fluff-based products, such as diapers and incontinence pads. The nonwoven web is typically bonded or consolidated in a fashion that gives it sufficient strength to be handled in the converting process. The web may also contain SAP particles.

The web consolidation mechanisms used in the roll-goods approach to making preformed cores provide strength and dimensional stability to the web. Such mechanisms include latex bonding, bonding with thermoplastic or bicomponent fibers or thermoplastic powders, hydroentanglement, needlepunching, carding, or the like.

One embodiment of a structure having an acquisition layer and a distribution layer (an "ADL") typically found on die-cut feminine hygiene pads is an airlaid cellulose web bonded with an aqueous binder resin that has been dried and cured. Airlaid materials typically retain up to 16 g of fluid per gram of material against gravity under negligible load. Thus, an ADL can acquire a surge of fluid within the absorbent product until the superabsorbent particles in the absorbent core can absorb the retained fluid out of the airlaid cellulose ADL and into final storage containing superabsorbent particles.

An example of a conventional airlaid cellulose material is Vicell 6002 (Buckeye Technologies Inc., Memphis Tenn.), which is a 105 gsm (grams per square meter) airlaid cellulose non-woven bonded with a vinyl acetate binder resin. Vicell 6002 is prepared by spraying an aqueous emulsion of the vinyl acetate binder resin onto the airlaid cellulose web followed by drying and curing in a hot air oven. It is used commercially in an ADL for feminine hygiene pads.

The disadvantage of certain commercially available airlaid cellulose structures is that they may collapse under normal use. This typically occurs when the structure is compressed by the weight of the wearer and particularly when the structure becomes wet. This structural collapse significantly reduces the fluid acquisition rate of the absorbent product and thus increases the chance of leakage. When a completely or partially fluid saturated airlaid cellulose structure collapses, the fluid escapes from the ADL and the product feels wet against the wearer's skin.

There is a need for thin absorbent core material which facilitates fluid transport from an acquisition zone to a storage zone, has a high absorbent capacity in use, and can be delivered in roll-goods form to simplify the manufacturing and converting processes.

Applicants have now surprisingly discovered an improved ADL containing at least two discrete layers, the top and the bottom layer, which overcomes the above-described disadvantage of commercially available products. The top layer (i.e., the layer in contact with the skin of wearer) of the ADL of the present invention is highly porous, thus preventing the collapse of the structure and minimizing the leakage problem.

SUMMARY OF THE INVENTION

The present invention provides a highly absorbent, high-bulk low density article having an absorbent structure comprising a liquid acquisition and, optionally, a distribution layer and a fibrous liquid storage layer in communication with the acquisition layer. The storage layer contains SAP particles, latex-bonded fibers, thermally bonded-fibers, or a combination thereof.

In one embodiment, the invention relates to an improved acquisition and distribution layer (ADL) having at least two layers for use in disposable absorbent products, a top (acquisition) layer in contact with the wearer of the absorbent product, and a bottom (distribution) layer between the top layer and a storage layer. Thus, according to one aspect of the invention, an improved ADL with a highly porous acquisition layer is provided.

In another aspect of the invention, an airlaid rolled good containing the ADL of the invention, and a method for its production is provided.

In yet another aspect of the invention, a disposable absorbent product containing the ADL of the invention, and a method for its production is provided.

The absorbent structure of the invention has the following advantages: (i) it is highly absorbent as it is made of a low-density material and has high-bulk properties; (ii) the layers are uniform due to the manner in which superabsorbent particles are deposited into the layers providing an absorbent web, and thus provide increased absorbent potential of the article; (iii) the absorbent article permits more economical means for providing an absorbent article because the function of multiple materials are combined into a single roll; and (iv) the wettability of the article can be adjusted as a result of (or by) surfactant addition during the acquisition layer forming process.

DETAILED DESCRIPTION OF THE INVENTION

All patents, patent applications, and literature references cited herein are hereby incorporated by reference in their entirety.

The present invention provides an improved fibrous absorbent structure which contains a liquid acquisition layer of lower density and a fibrous storage layer of relatively higher density. The structure is a composite including at least these two layers which confer upon the structure the ability to acquire and distribute fluids through the density gradient. The acquisition layer is capable of rapidly acquiring liquid from insult. The storage layer absorbs and stores the liquid acquired from the acquisition layer.

In addition, the invention preferably contains a distribution layer, which in combination with the fluid acquisition layer provides an improved ADL, containing at least two layers, a top acquisition layer and a distribution layer. When used in a disposable absorbent product, the acquisition layer is closer to the skin of the wearer and away from the storage layer; the distribution layer is closer to the storage layer and away from the skin of the wearer. The acquisition layer provides rapid fluid acquisition under load. The distribution layer provides z-direction capillary force to pull fluid into the absorbent storage layer, away from the skin of the wearer, to provide temporary fluid immobilization, and to act as a conduit for fluid drawn into the unsaturated portion of the storage layer. The absorbent structure of the invention has high absorbent capacity and is particularly useful as an absorbent core for disposable absorbent articles such as diapers, adult incontinence pads and briefs, and feminine sanitary napkins, and the like.

The fiberized fluff cellulose fibers used in the ADL or storage layer of the composite structure of the present invention may be selected from wood cellulose such as Foley fluff, cotton linter pulp, chemically modified cellulose such as crosslinked cellulose fibers or highly purified cellulose fibers, such as Buckeye HPF.

The present invention makes use of the unexpected discovery that a latex-bonded, synthetic fiber in the acquisition layer provides an absorbent structure having improved acquisition and retention characteristics (i.e., absorbency) compared with an absorbent structure employing an acquisition layer lacking such fibers. The advantage of using synthetic fibers is that such fibers maximize the surface dryness of the absorbent product. Any synthetic fiber, including polyester fibers, such as polyethylene terepthalate (PET), polypropylene, nylon and acrylic, and combinations thereof, may be used provided that the fiber has the property of forming large pores resistant to collapse when the layer is wet.

The melting point of the synthetic fiber should be taken into consideration during the manufacturing process and the temperature should be adjusted to avoid melting of the fiber. For purposes of the present disclosure, "large pore" means a pore larger, and more resistant to collapse, than the pore formed by cellulose fibers. Because large pores contained within a synthetic fiber matrix resist collapse under pressure when wet, the top layer can rapidly acquire a surge of fluid as it passes through the liner or top sheet of the absorbent product. The size of the pore will depend on the composition of the fiber, size of the fiber (i.e., fiber diameter), resiliency of the fiber, and resiliency of the latex. A person of skill in the art may optimize the pore size to suit any particular need using general knowledge in the art (see, for example, U.S. Pat. Nos. 5,569,226 and 5,505,719 issued to Cohen) and routine experimentation.

The synthetic fibers of the top layer are bonded with an aqueous dispersion (emulsion) of a natural or a synthetic polymer latex. Any latex may be used in the invention. The synthetic polymer may be, for example, a polymer or copolymer of alkylacrylates, vinyl acetate, or styrene-butadiene. Other polymers known in the art may be used. For purposes of industrial hygiene and elimination of a solvent recycling step, the synthetic latexes can be applied as an aqueous based emulsion rather than an organic solvent emulsion. In the present invention, the preferred matrix fibers of the acquisition layer are 3 to 20 denier crimped PET fibers with a cut length of 3 to 15 mm.

The distribution layer of the improved ADL preferably contains latex and/or thermal bonded cellulose fibers. Any fluff cellulose fibers may be used in this layer, preferably wood fibers such as airlaid-fluff cellulose, chemically modified cellulose fibers, (e.g., cross-linked cellulose fibers), highly purified cellulose, cotton linter fibers, or blends thereof. For bonding purposes, the latex dispersions used for bonding the fibers of the top layer may be used. Alternatively, or in combination with a latex binder, thermoplastic fibers or powder may be used for bonding upon heating to the melting point of the thermoplastic fiber or powder. Bicomponent fibers having a PET core surrounded by a polyethylene sheath, e.g., Hoechst-Trevira Type-255 (Charlotte, N.C.), and polyethylene powder may be used.

The distribution layer of the improved ADL provides both a temporary retention zone and a liquid distribution channel into the final storage layer. The cellulose fibers of this layer form a microporous medium that spontaneously distributes fluid from the point of fluid insult to unsaturated portions of the distribution layer via a combination of surface tension driving force and gravity. Once the spreading fluid from insult contacts an unsaturated portion of the storage layer, which has a higher surface tension than the ADL, the fluid within the distribution layer flows into the storage layer until a surface tension equilibrium is reached. The higher surface tension of the storage layer can be generated by providing higher density cellulose fiber and/or superabsorbent particles. Thus the distribution layer becomes both a fluid reservoir for, and a flow channel to, the storage layer. The flow channel function is particularly important in certain thin absorbent pads where the ADL covers a significantly greater surface area than the absorbent core or storage layer.

Optionally, other ingredients such as surfactants, pigments, and opacifiers may be added to the acquisition or distribution layers without affecting absorbency.

The basis weight of the ADL layer of the invention may range from about 30 to 150 gsm, preferably from about 60 to 100 gsm, and most preferably about 80 gsm. In one embodiment, the basis weight of each of the acquisition and the distribution layer of the ADL may range from about 15 to 60 gsm. Preferably, the basis weight of each layer is at minimum about 25% of the total ADL basis weight. In one embodiment, the top layer is from about 25 to 50% of the total ADL basis weight.

The ADL of the present invention may contain an optional middle layer. The middle layer may contain 100% fluff cellulose and/or chemically modified cellulose fibers or have a fiber composition that is a blend of synthetic fibers and cellulose fibers.

In one embodiment of the ADL, the acquisition layer contains about 80–90% by weight of 6.7 dtex (wt/length of fiber) in size by 6 mm in cut length polyester (PET) fiber bonded with 10–20% by weight of an aqueous binder resin. The bottom layer contains 80–90% of fiberized fluff cellulose fibers that are bonded using 10–20% of an aqueous binder. The fiberized fluff cellulose fibers may contain wood cellulose such as Buckeye Foley fluff (Buckeye Technologies Inc.), cotton linter pulp such as Buckeye HPF (Buckeye Technologies Inc.), or chemically modified cellulose such as cross-linked cellulose fibers. In another embodiment, the top and bottom layers of the ADL are as above, but a middle layer containing a blend of PET and cellulosic fibers is also present. In this embodiment the top layer is at least 10% of the total ADL weight and the bottom layer is no more than 50% of the total ADL basis weight.

The preferred overall basis weight range of the composite absorbent structure of the invention is 100–500 grams per square meter (gsm). The composite absorbent structures include a fluid acquisition layer and a fluid distribution layer (described above) and a fluid storage layer. The fluid storage layer is below the fluid distribution layer and is comprised of a fluff cellulose or chemically modified fluff cellulose matrix fibers, a superabsorbent polymer (SAP), and a bonding element. The bonding element is preferably bicomponent fibers in the concentration of 5 to 20% but may also include thermoplastic powders. Preferably, the SAP content is 10–70% by weight of the absorbent structure.

As used herein, "superabsorbent polymer" or "SAP" means any suitable hydrophilic polymer that can be mixed with fibers of the present invention. A superabsorbent polymer is a water soluble compound that has been cross-linked to render it water insoluble but still swellable to at least about 15 times its own weight in physiological saline solution. These superabsorbent materials generally fall into 3 classes, namely starch graft copolymers, cross-linked carboxymethylcellulose derivatives, and modified hydrophilic polyacrylates. Examples of absorbent polymers include hydrolyzed starch-acrylontrile graft co-polymer, saponified acrylic acid ester-vinyl co-polymer, modified cross-linked polyvinyl alcohol, neutralized cross-linked polyacrylic acid, cross-linked polyacrylate salt, and carboxylated cellulose. The preferred superabsorbent materials, upon absorbing fluids, form hydrogels.

The superabsorbent polymer materials have relatively high gel volume and relatively high gel strength as measured by the shear modulus of the hydrogel. Such preferred materials also contain relatively low levels of polymeric materials which can be extracted by contact with synthetic urine. Superabsorbent polymers are well-known and are commercially available. One example is a starch graft polyacrylate hydrogel marketed under the name IM1000 (Hoechst-Celanese, Portsmouth, Va.). Other commercially available superabsorbent polymers are marketed under the trademark Sanwet (Sanyo Kasei Kogyo Kabushiki, Japan), Sumika Gel (Sumitomo Kagaku Kabushiki Haishi, Japan), Favor (Stockhausen, Garyville, La.) and the ASAP series (Chemdal, Aberdeen, Miss.). Superabsorbent particulate polymers are also described in detail in U.S. Pat. No. 4,102,340 and U.S. Pat. No. Re. 32,649. An example of a suitable SAP is surface cross-linked acrylic acid based powder such as Stockhausen 9350 or SX FAM 70 (Greensboro, N.C.).

The preferred basis weight range(s) and SAP content may vary with the intended application. For feminine hygiene and light capacity adult incontinence applications, for example, the basis weight and SAP content will tend to be toward the lower end of the ranges indicated in Table 1. For infant diaper and heavy capacity adult incontinence applications, the preferred basis weight and SAP content will tend to be toward the high end of the specified range in Table 1.

Multiple matrix fibers can be used in an absorbent article of the invention, however, it is preferred that collectively the matrix fibers constitute most of the fibers in the material (e.g., at least 75%). The term matrix fiber as used herein, refers to a synthetic or cellulosic fiber that does not melt or dissolve to any degree during the forming or bonding of an air-laid absorbent structure. The terms "thermal bonding" or "thermal" herein refer to the blending of thermoplastic material (e.g., bonding methods listed in Table 1) in which the matrix fiber(s) and SAP bond the absorbent layers when heat is applied.

Examples of suitable thermoplastic materials include thermoplastic microfibers, thermoplastic powders, bonding fibers in staple form, and bicomponent staple fibers. Bicomponent staple fibers are characterized by a high melt temperature core polymer (typically polyethylene terephthalate (PET) or polypropylene) surrounded by a low melt temperature sheath polymer (typically polyethylene, modified polyethylene, or copolyesters). In the preferred embodiments of this invention, bicomponent fibers provide the means of thermal bonding.

Table 1 provides a general outline of an embodiment of the invention.

TABLE 1

| Layer | Matrix Fiber | SAP % | Bonding Method | Basis Wt Range (gsm) |
|---|---|---|---|---|
| Acquisition | Polyester (PET) and/or polyolefin homopolymer fibers | None | Latex binder | 20–80 |
| Distribution | Fluff cellulose and/or chemically modified cellulose fiber | None | Thermal and/or latex binder | 20–100 |
| Storage | Fluff cellulose and/or chemically modified cellulose fiber | 10–75 | Thermal | 60–400 |

In one embodiment for feminine hygiene and light adult incontinence products, the absorbent product of the invention contains an acquisition layer, a distribution layer and a storage layer, having a total basis weight of 120 gsm to 290 gsm. The acquisition layer, comprising latex bonded PET matrix fibers, has a 20 to 60 gsm total basis weight. The matrix fibers are 6 to 15 denier in size, 3 to 12 mm in length and have 2 to 5 crimps/cm. The latex is an emulsion of ethylene vinyl acetate, styrene-butadiene, or acrylic polymer. The latex binder is about 5 to 25% of the weight of the acquisition layer. The distribution layer, comprising thermal bonded fluff cellulose or chemically modified fluff cellulose fibers, has a 30 to 90 gsm total basis weight. The cellulose fiber is thermally bonded with 5 to 20% by weight of sheath/core bicomponent fiber (e.g., 3 denier T-255 bicomponent fiber from Hoechst-Celanese, Charlotte, N.C.). The storage layer of thermal bonded fluff cellulose with 20 to 50% SAP has a 70 to 130 gsm total basis weight. The fluff cellulose/SAP mixture is thermally bonded with 5 to 10% by weight of sheath/core bicomponent fiber. Specific embodiments are described in Examples 3, 9, 14, 15, 16.

In another embodiment, which can be employed in infant diapers and heavy adult incontinence products, the acquisition layer, distribution layer, and storage layer have a total basis weight of 300 gsm to 500 gsm. The acquisition layer, comprising latex bonded PET matrix fibers, has a 20 to 60 gsm total basis weight. The matrix fibers are 6 to 15 denier in size, 3 to 12 mm in length and have 2 to 5 crimps/cm. The latex is an emulsion of ethylene vinyl acetate, styrene-butadiene, or acrylic polymer, and is about 5 to 25% of the weight of the acquisition layer. The distribution layer, comprising thermally bonded fluff cellulose or chemically modified fluff cellulose fibers, has a 30 to 100 gsm total basis weight. The cellulose fiber is thermally bonded with 5 to 20% by weight of sheath/core bicomponent fiber. The storage layer of thermally bonded fluff cellulose with 40 to 75% SAP has a 250 to 340 gsm total basis weight. The fluff cellulose/SAP mixture is thermally bonded with 5 to 10% by weight of sheath/core bicomponent fiber. Specific embodiments are described in Examples 8 and 10.

An absorbent article of the invention can be made in one continuous process utilizing air forming equipment such as equipment sold by M&J Fibertech (Horsens, Denmark) or Dan-Web (Aarhus, Denmark). The bottom or cellulose fiber layer is formed onto a moving collection wire, and the synthetic fiber layer is airlaid directly on top of the cellulose fiber layer. The resulting composite structure is then passed under an adhesive application station (typically a set of spray nozzles or foam coater) that applies adhesive directly onto the synthetic fiber layer. The material then travels through a hot air oven, or other suitable heating device, to bond the structure. In the preferred embodiments, adhesive is next applied to the cellulose fiber side of the composite structure and the material is passed through a second oven to dry the adhesive. A third heating station may be employed to insure that the adhesive is fully cured. The absorbent structure of the invention may be finally packaged and shipped in roll-goods form.

Preferably, the absorbent structures of the invention are prepared as an airlaid web. The composite material may be manufactured in a continuous operation provided the production line has at least three separate forming heads, a synthetic fiber dosing system capable of handling at least two different synthetic fibers simultaneously, a superabsorbent powder dosing system and a latex adhesive application system.

The airlaid web is typically prepared by disintegrating or fiberizing a cellulose pulp sheet or sheets, typically by hammermill, to provide individualized fibers. The individualized fibers are then air conveyed to forming heads on the airlaid web forming machine. The forming heads include rotating or agitated drums, generally in a race track configuration which serve to maintain fiber separation until the fibers are pulled by vacuum onto a foraminous condensing drum or foraminous forming conveyor (or forming wire). In the M&J machine, the forming head includes a rotary agitator above a screen. Other fibers, such as a synthetic thermoplastic fiber, may also be introduced to the forming head through a fiber dosing system which includes a fiber opener, a dosing unit and an air conveyor. Where two defined layers are desired, such as a fluff pulp distribution layer and a synthetic fiber acquisition layer, two separate forming heads are provided, one for each type of fiber.

The airlaid web is transferred from the forming wire to a calender or other densification stage to densify the web, increase its strength and control web thickness. The fibers of the web are then bonded by application of a latex spray or foam addition system, followed by drying or curing. Alternatively, or additionally, any thermoplastic fiber present in the web may be softened or partially melted by application of heat to bond the fibers of the web. The bonded web may then be calendered a second time to increase strength or emboss the web with a design or pattern. If thermoplastic fibers are present, hot calendering may be employed to impart patterned bonding to the web. Water may be added to the web if necessary to maintain specified or desired moisture content, to minimize dusting, or to reduce the buildup of static electricity. The finished web is then rolled for future use.

In one embodiment (e.g., Example 1) the acquisition and distribution layer are air formed independent of the fluid storage layer. The composite acquisition/distribution layer is combined with the storage layer at the converting line. This embodiment is useful for absorbent product designs where the storage layer covers a different area than the acquisition/distribution layer. Other embodiments of this type are described in Examples 11, 12, and 13.

The following non-limiting Examples further describe the invention, the scope of which is to be limited only by the claims.

EXAMPLE 1–2

To test the acquisition rate of fluid using an ADL of the invention, samples having a target basis weight of 80 gsm were formed on a laboratory air forming device. The top layer of Example 1 contained 34 gsm of 6.7 dtex, 6 mm long polyester (PET) fibers (Hoechst Trevira, Charlotte, N.C.) and 6 gsm of AirFlex 192 latex binder (Air Products and Chemicals, Allentown, Pa.). The bottom layer contained 34 gsm Buckeye Foley fluff pulp and 6 gsm AirFlex 192 latex binder. A control sample, Example 2, was prepared on the same laboratory air forming device containing a single layer having a basis weight of 80 gsm, comprising 68 gsm Buckeye Foley fluff wood cellulose fibers and 12 gsm Air Flex 192. The Foley fluff cellulose is typical of the fiber employed in conventional airlaid acquisition layers such as Vicell 6002 (Buckeye Technologies Inc.).

Each sample was placed on a two-ply Zorbcore 5901 (Buckeye Technologies Inc.), which includes a 250 gsm thermal bonded airlaid Foley fluff material containing 25% Stockhausen SX FAM 70 SAP. The ADL/absorbent core stack was covered with an 18 gsm polypropylene top sheet. Test and control samples for 3 separate measurements (each sample having the dimensions of 25 cm×10 cm) were prepared. Each sample was wrapped with an appropriate coverstock material and placed on the bottom fluid intake test ("FIT") board with the wire or carrier side facing down. The center of the samples was marked.

Acquisition rate evaluations were made by subjecting test samples to three consecutive 50 ml insults of 0.9% saline solution. The first insult of 50 ml 0.9% saline solution was poured into the clear addition tube of the FIT board as fast as possible, without overflowing. The time from the moment of pouring until the saline reached the test sample was measured. The stopwatch was stopped as soon as all of the saline passed from the bottom edge of the tube. The recorded time was the time required for acquisition by the top layer. After one minute intervals, the procedure was repeated with a second and third 50 ml insult.

The acquisition rate from each fluid insult was determined according to the following formula:

Acquisition Rate (ml/s)=volume of fluid insult (ml)/acquisition time(s)

The acquisition rate results are represented in Table 2 as milliliters per second (ml/s) of fluid penetration through the top sheet.

the fluid acquisition rate relative to the control sample consisting of a single layer lacking PET for each of the three insults.

Another critical function of an ADL is to isolate the wearer of the absorbent product from the fluid contained within the absorbent product. While a low density airlaid cellulose layer may have very rapid fluid acquisition, the cellulose fibers of a conventional airlaid ADL often retain fluid or provide a conduit for fluid to leak out of the core when the ADL is under pressure, thus making the wearer's skin wet. In contrast, the synthetic fibers of the top layer of the present ADL create large pores so that, even under pressure, the top layer neither retains fluid nor provides a conduit for fluid to leak from the distribution or storage layers toward the wearer. This advantage is experimentally shown in the present example.

The test samples described in Example 1 were placed on top of a two-ply Zorbcore 5901, below the 18 gsm non-woven top sheet. This stack of materials was tested according to the rewet/fluid retention test described, supra, by measuring the amount of 0.9% saline solution that could be absorbed back through the top sheet by a stack of filter paper under 0.1 psi pressure after each fluid insult. Test and control samples for 3 separate measurements (each measuring 8½"× 11") were prepared. Each sample was placed onto the plastic platform with tissue side down and its center was marked. Fifty ml of 0.9% saline solution (first insult) was drained onto the sample from a funnel from a distance of approximately 1.5" above the center of the sample. The sample was allowed to sit for 20 minutes. A stack of 12 filter papers was weighed and placed on the center of the wetted area and pressed by a circular weight on top. After 2 minutes the wet filter papers were removed and weighed again. This procedure was repeated with a second insult of 50 ml saline and a stack of 16 filter papers, and a third insult of 50 ml saline and a stack of 20 filter papers. The rewet value and the percent fluid retention was calculated for the first, second and third insults according to the following formulas:

Rewet$_{1,2or3}$=Wet filter papers weight–Dry filter papers weight %
Retention=(50–Rewet)50×100%

TABLE 2

| | | Acquisition Rate | | | | |
|---|---|---|---|---|---|---|
| | | 50 ml ACQUISITION RATE | | | ADL Fiber | |
| | units | 1st Insult | 2nd Insult | 3rd Insult | Composition | Core |
| Ex. 1 | ml/sec | 7.36 | 2.29 | 1.95 | PET/Foley Fluff | 2 ply Zorbcore 5901 |
| Ex. 2 | ml/sec | 3.23 | 1.15 | 0.86 | Foley Fluff | 2 ply Zorbcore 5901 |

The results show that the sample containing the bilayer of latex-bonded PET/Foley fluff (i.e., the ADL prepared according to the present invention) had approximately twice The results are represented in Table 3 as a percentage of each 50 ml fluid insult that was retained by the core after the filter paper was removed.

TABLE 3

| | | Fluid Retention Results | | | | |
|---|---|---|---|---|---|---|
| | | 50 ml FLUID RETENTION (%) | | | ADL Fiber | |
| | 1st Insult | 2nd Insult | 3rd Insult | Composition | Core |
| Ex. 1 | 99.46% | 89.92% | 63.64% | PET/Foley Fluff | 2 ply Zorbcore 5901 |
| Ex. 2 | 97.74% | 62.24% | 33.96% | Foley Fluff | 2 ply Zorbcore 5901 |

The latex bonded PET/Foley fluff cellulose bilayer (i.e., the ADL prepared according to the present invention) had a significantly higher fluid retention than the sample containing only latex-bonded fluff cellulose.

EXAMPLES 3–4

To test the absorbent core of the invention in combination (Example 3) a composite absorbent core was created by first air forming a layer of 100% 6 denier×6 mm long PET fibers on top of preformed Vizorb X479 material (Buckeye Technologies Inc.). The PET fiber layer was then bonded in place by spraying a 15% by weight aqueous solution of AirFlex 192 latex binder (Air Products & Chemicals, Allentown, Pa.). The Vizorb X479 is a latex/thermal bonded absorbent core fluff cellulose that contains 30% SAP (Stockhausen SX FAM 70; Greensboro, N.C.). Vizorb X479 also has a SAP-free top layer containing thermal-bonded Buckeye HDF chemically modified fluff cellulose that becomes the fluid distribution layer once the latex bonded acquisition layer is formed on top of the X479 material. A 15 gsm cellulose tissue carrier sheet was provided below the bottom surface of the Vizorb X479 material for SAP containment during the web forming process to prevent fouling of the equipment due to SAP separating from the structure. The target composition and configuration of the absorbent structure of Example 3 is shown in Table 4. This preparation was repeated using a composite absorbent core formed from a layer of 100% 6 den×12 mm PET fibers.

The fluff cellulose fiber in the distribution and storage layers was 67% Buckeye Foley Fluff and 33% Weyerhaeuser PD 416 (Seattle, Wash.) by weight. The bicomponent fiber used was 3.1 dtex×4 mm long Hoechst-Trevira T-255 (Charlotte, N.C.), the SAP powder was Stockhausen SX-70 (Greensboro, N.C.), and the latex binder resin was AirFlex 124 (Air Products). The term "dtex" refers to the mass, in grams, of 10,000 meters of fiber. The term "denier" refers to the mass, in grams of 9,000 meters of fiber.

The acquisition layer matrix fiber of Example 3a contained Hoechst-Trevira Type-224 crimped 6.7 dtex by 6 mm long polyester (polyethylene terephthalate or PET), and AirFlex 192 latex resin. Example 3b was identical to 3a except that the length of the PET fiber was 12 mm. The binder for the fluff cellulose acquisition layer was AirFlex 192 and the fluff cellulose was 100% Buckeye Foley fluff.

A reference sample (Example 4) was created by air forming a 40 gsm layer of Foley fluff cellulose onto Vizorb X479 material. The fluff cellulose was then latex bonded as in Example 1. The reference sample exemplifies a conventional air formed structure lacking PET fiber. Table 5 shows the target composition and configuration of the reference sample.

TABLE 5

|  | Fluff Cellulose (gsm) | Bonding Fiber (gsm) | SAP Powder (gsm) | Latex Binder Resin (gsm) | PET Fiber (gsm) |
| --- | --- | --- | --- | --- | --- |
| Acquisition Layer | 34.0 | none | none | 6.0 | none |
| Distribution Layer | 30.3 | 3.5 | none | 1.3 | none |
| Storage Layer | 64.1 | 7 | 52.5 | 1.3 | none |

The test and control samples for three separate measurements were further prepared as in Example 1. Acquisition rate evaluations were made by subjecting the composite structures of Examples 3a, 3b and 4 by subjecting the samples to three consecutive insults as described in Example 1–2.

The acquisition rate results are represented in Table 6 as milliliters per second of fluid penetration through the top sheet.

TABLE 6

|  | Acquisition Rate (ml/s) | | | |
| --- | --- | --- | --- | --- |
|  | 1st Insult | 2nd Insult | 3rd Insult | Fiber |
| Ex. 3a | 2.27 | 1.05 | 0.58 | PET (6 mm) |
| Ex. 3b | 2.13 | 1.12 | 0.68 | PET (12 mm) |
| Ex. 4 | 0.79 | 0.32 | 0.12 | Foley |

Table 6 shows that the samples having latex-bonded PET acquisition layer has a 300 to 400 percent greater fluid acquisition rate than the sample having a latex-bonded fluff cellulose acquisition layer.

The structures of Examples 3a, 3b, and 4 were also subjected to liquid rewet/retention testing with 50 ml saline insults as in Example 1–2. The rewet value and the percent liquid retention was calculated for the first, second and third insults according to the rewet formulas of Example 2. The results are represented in Table 7 which shows the amount of liquid in grams that could be pulled through the top sheet with filter paper.

TABLE 4

|  | Fluff Cellulose (gsm) | Bonding Fiber (gsm) | SAP Powder (gsm) | Latex Binder Resin (gsm) | PET Fiber (gsm) |
| --- | --- | --- | --- | --- | --- |
| Acquisition Layer | none | none | none | 6.0 | 34.0 |
| Distribution Layer | 30.3 | 3.5 | none | 1.3 | none |
| Storage Layer | 64.1 | 7 | 52.5 | 1.3 | none |

TABLE 7

50 ml REWET

| | units | 1st Insult | 2nd Insult | 3rd Insult | Fiber |
|---|---|---|---|---|---|
| Ex. 3a | grams | 0.17 | 0.97 | 2.21 | PET (6 mm) |
| Ex. 3b | grams | 0.09 | 0.45 | 0.78 | PET (12 mm) |
| Ex. 4 | grams | 0.19 | 4.5 | 10.33 | Foley |

Table 8 shows the results of Table 7 expressed as a percentage of each 50 ml liquid insult that was retained by the core after the filter paper was removed.

TABLE 8

50 ml LIQUID RETENTION (%)

| | 1st Insult | 2nd Insult | 3rd Insult | Composition |
|---|---|---|---|---|
| Ex. 3a | 99.66 | 98.06 | 95.58 | PET (6 mm) |
| Ex. 3b | 99.82 | 99.10 | 98.44 | PET (12 mm) |
| Ex. 4 | 99.62 | 91.00 | 79.34 | Foley |

Tables 7 and 8 show that the latex-bonded PET acquisition layer yields significantly better fluid retention than a conventional latex bonded fluff cellulose acquisition layer.

EXAMPLES 5–8

In this embodiment of the invention, a layer of 6 den×6 mm PET matrix fiber was bonded using a combination of latex bonding and thermal bonding, i.e., multibinding-a combination of two types of bonding techniques). The first step was to form an airlaid absorbent core designated DL-1. The basis weight of the DL-1 material was 425.0 gsm. The DL-1 material included a SAP/fluff cellulose fluid storage layer on a 15 gsm tissue carrier and a distribution layer which contained predominantly airlaid Buckeye HPF (chemically purified cellulose fiber having a small percentage of bicomponent fibers). The DL-1 storage layer included 144.9 gsm of fluff pulp and 153 gsm of Stockhausen 9350 SAP. The distribution layer of the DL-1 material included 48.6 gsm of Buckeye HPF fiber. In addition, 46.6 gsm of bicomponent thermal fiber was distributed throughout the core and distribution layers of the DL-1 material. The distribution layer and storage (core) layers were thermally bonded with a small amount of latex sprayed in dilute aqueous solution (17 gsm solids), such that the layers contained SAP particles and cellulose fibers.

The DL-1 material 5 was collected on a roll and a portion of the roll was passed back through an M&J web forming and bonding system (Horsens, Denmark). An acquisition layer was air formed on top of the distribution layer of the DL-1 material. For each sample, the acquisition layer was applied by blending the matrix fiber with the bicomponent fiber and airforming the layer onto the DL-1 material (see Table 9). The matrix fibers Buckeye HPF and Buckeye HPZU are chemically purified cellulose fibers. The bicomponent fiber was T 255 fiber (Hoechst-Trivera). The latex was AirFlex 192 (Air Products).

TABLE 9

| Ex. | Matrix Fiber | Basis Weight | Bico Fiber | Latex | Total |
|---|---|---|---|---|---|
| 5 | Buckeye HPF | 61.6 | 2.8 | 5.6 | 70.0 |
| 6 | Buckeye HPZU | 69.5 | 7.2 | 13.5 | 90.3 |
| 7 | cross-linked cellulose | 69.3 | 7.2 | 13.5 | 90.0 |
| 8 | H-T 6.7 dtex PET | 54.6 | 5.2 | 5.2 | 65.0 |

The airlaid, multibonded structures of Table 9 were subjected to liquid acquisition rate testing according to the method described for Example 1. The results are set forth in Table 10.

TABLE 10

Fluid Acquisition Rate (ml/sec)
Multiple 50 ml Insults

| Ex. | 1st Insult | 2nd Insult | 3rd Insult |
|---|---|---|---|
| 5 | 6.76 | 2.05 | 1.37 |
| 6 | 4.46 | 2.03 | 1.39 |
| 7 | 5.95 | 2.28 | 1.68 |
| 8 | 7.69 | 3.79 | 2.81 |

The fluid acquisition rate of the sample material of Example 8, which contained an acquisition layer of latex bonded Polyester (PET) fibers, exhibited the highest liquid acquisition rate.

The airlaid, multibonded structures of Examples 5–8 were subjected to liquid retention testing according to the method of Example 2. The results are set forth in Table 11.

TABLE 11

50 mL Liquid Retention (%)

| Ex. | 1st Insult | 2nd Insult | 3rd Insult |
|---|---|---|---|
| 5 | 96.9 | 57.8 | 39.1 |
| 6 | 94.5 | 50.9 | 37.7 |
| 7 | 98.7 | 65.8 | 52.7 |
| 8 | 99.8 | 95.2 | 90.3 |

Table 11 shows that the sample material of Example 8, which contained a PET fiber acquisition layer, had a significantly higher percentage of fluid retained under pressure in the composite structure compared with the other structures employing cellulose-based acquisition layers (Examples 5–7).

EXAMPLES 9–10

Examples 9 and 10 are specific embodiments of the three layer invention optimized for thin sanitary pads and light adult incontinence applications (Example 9), and for infant diaper/training pant applications (Example 10).

EXAMPLE 9

A sample was produced on a M&J type air forming line with a target composition and configuration as described in Table 12. The storage layer was made from Foley fluff cellulose (Buckeye Technologies Inc.) and the distribution layer from HPF fluff cellulose (Buckeye Technologies Inc.). The binding fiber employed was T-255 3 den×4 mm (Hoechst-Trevira). The synthetic matrix fiber employed was (Type D2645 6 den×6 mm crimped (4.2 cr/cm) PET fiber (Hoechst-Trevira). The SAP used was Stockhausen type 9350. The sample material was formed onto an 18 gsm tissue sheet to prevent contamination of the air forming equipment with particles of superabsorbent powder. This three layer structure plus carrier tissue was thermally bonded and compacted to achieve an overall material density of 0.094 g/cc and basis weight of 219 gsm. The resulting ADL/core absorbent material is one embodiment of the invention which can be used for thin sanitary pads and light adult incontinence applications.

TABLE 12

|  | Fluff Cellulose (gsm) | Bonding Fiber (gsm) | SAP Powder (gsm) | Latex Binder Resin (gsm) | Pet Fiber (gsm) |
|---|---|---|---|---|---|
| Acquisition Layer | none | none | none | 6.0 | 34.0 |
| Distribution Layer | 57 | 3 | none | none | none |
| Storage Layer | 55 | 5 | 40 | none | none |

The sample was tested against two commercially available (N. America and European brand A) thin sanitary pads for both fluid acquisition and retention according to the methods of Examples 1 and 2, except that the amount of each fluid insult was 10 ml. The results are shown in Table 13. The weight basis is a sum of the multiple absorbent components that made up the fluid acquisition, distribution, and storage layers of a product.

TABLE 13

|  | ADL/Core Basis Wt. (gsm) | Acquisition Rate (ml/sec) 10 ml saline insults | | | Fluid Retention (%) 10 ml saline insults | | |
|---|---|---|---|---|---|---|---|
|  |  | $1^{st}$ Insult | $2^{nd}$ Insult | $3^{rd}$ Insult | $1^{st}$ Insult | $2^{nd}$ Insult | $3^{rd}$ Insult |
| Example 9 | 219 | 4.5 | 2.3 | 1.9 | 98 | 92 | 74 |
| European | 240 | 3.5 | 0.7 | 0.5 | 79 | 45 | 27 |
| N. American | 250 | 0.9 | 0.3 | 0.2 | 99 | 67 | 32 |

EXAMPLE 10

A sample was produced in the same manner as the sample in Example 9, in accordance with Table 14, except that the fluff cellulose in the storage layer was ND-416 (Weyerhaeuser, Tacoma, Wash.) and the fluff cellulose in the distribution layer was Foley fluff (Buckeye Technologies Inc.). The overall material density was 0.117 g/cc and basis weight was 504 gsm.

TABLE 14

|  | Fluff Cellulose (gsm) | Bonding Fiber (gsm) | SAP Powder (gsm) | Latex Binder Resin (gsm) | Synthetic Matrix Fiber (gsm) |
|---|---|---|---|---|---|
| Acquisition Layer | none | none | none | 8.0 | 42.5 |
| Distribution Layer | 85 | 15 | none | none | none |
| Storage Layer | 105 | 15 | 180 | none | none |

Sample 1 was tested against two commercially available infant diapers and training pants for both fluid acquisition and retention according to the methods of Examples 1 and 2. The results are shown in Table 15. The basis weights of the acquisition, distribution and storage components of the commercial products were as follows: A, 622 gsm; B, 792 gsm; C, 522 gsm; and D, 840 gsm.

TABLE 15

|  | Multiple Saline Insults Acquisition Rate | Multiple Saline Insults Fluid Retention (%) | | |
| --- | --- | --- | --- | --- |
|  | 3$^{rd}$ Insult | 1$^{st}$ Insult | 2$^{nd}$ Insult | 3$^{rd}$ 50 ml Insult |
| Example 10 | 4.0 | 99.9 | 97.0 | 87.0 |
| A | 2.4 | 99.9 | 96.8 | 79.8 |
| B | 1.8 | 99.9 | 99.0 | 95.9 |
| C | 2.9 | 99.5 | 96.9 | 87.3 |
| D | 2.5 | 96.4 | 79.1 | 57.2 |

EXAMPLES 11–13

These examples show three embodiments of an ADL of the invention on a preformed and bonded absorbent core (see Table 16). The embodiments compare the effect of matrix fiber size over the range of 6 to 15 denier. The distribution layer in Example 13 has a combination of latex and thermal bonding.

EXAMPLE 11

The two layer ADL was formed in the same manner as in Example 1, in accordance with Table 16, using Foley fluff cellulose in the distribution layer (Buckeye Technologies Inc.), T 255 3 den×4 mm bonding fiber (Hoechst-Trevira), AirFlex 192 latex binder (Air Products), D2645 PET 6 den×6 mm×4.2 cr/cm synthetic matrix fiber (Trevira) to form an 18 gsm wet laid tissue product.

EXAMPLE 12

In this example an ADL was formed as in Example 11, except that the synthetic matrix fiber utilized in the acquisition layer was Trevira D2670 PET synthetic matrix fiber (9 den×6 mm×3.9 cr/in).

EXAMPLE 13

In this example an ADL was formed as in Example 11, except that the synthetic matrix fiber utilized in the acquisition layers was Trevira D2660 PET synthetic matrix fiber (15 den×6 mm×3.2 cr/cm).

The samples from Examples 11–13 were placed over Buckeye Airlaid grade 5901 cores (Buckeye Technologies Inc.) and tested for fluid acquisition rate and fluid retention according to the methods of Examples 1 and 2. The 5901 material is a thermally bonded uniformly blended materials containing 25% Stockhausen SX FAM 77 superabsorbent powder, 10% Trevira T-255 bicomponent fiber, 6% tissue carrier sheet, and 59% Weyerhaeuser Super Soft Ultra fluff cellulose.

The results in Table 17 show that the 9 den PET fiber employed in Example 12 provided the maximum fluid acquisition rate; fluid retention was not significantly effected by the choice of matrix fiber in these examples.

TABLE 16

|  | Fluff Cellulose (gsm) | Bonding Fiber (gsm) | SAP Powder (gsm) | Latex Binder Resin (gsm) | Synthetic Matrix Fiber (gsm) |
| --- | --- | --- | --- | --- | --- |
| Acquisition Layer | none | none | none | 4.0 | 22.6 |
| Distribution Layer | 37.3 | 15 | none | 8.0 | none |

TABLE 17

|  | Acquisition Rate (ml/sec) Multiple 50 ml Saline Insults | | | Fluid Retention (%) Multiple 50 ml Saline Insults | | |
| --- | --- | --- | --- | --- | --- | --- |
|  | 1$^{st}$ Insult | 2$^{nd}$ Insult | 3$^{rd}$ Insult | 1$^{st}$ Insult | 2$^{nd}$ Insult | 3$^{rd}$ Insult |
| Example 11 | 14.2 | 6.5 | 5.5 | 71.7 | 87.0 | 89.0 |
| Example 12 | 15.0 | 7.2 | 6.7 | 70.1 | 85.7 | 86.5 |
| Example 13 | 10.7 | 5.8 | 5.0 | 78.6 | 88.3 | 90.0 |

EXAMPLES 14–16

These Examples compare various latex bonders used in the acquisition layers. In Examples 14–16, the latex bonded PET acquisition layer was formed onto a Vizorb X479 absorbent core (Buckeye Technologies Inc.) (See Example 3). The configuration of the absorbent samples is set forth in Table 18.

EXAMPLE 14

The fluff cellulose used in the distribution layer and in the storage layer was HPF and Foley fluff, respectively (Buckeye Technologies Inc.). The bonding fiber was T-255 3 den×4 mm (Hoechst-Trevira). The latex binder was AirFlex 192 (Air Products). The synthetic matrix fiber was Type D2645 PET 6 denier×6 mm×4.2 cr/cm (Trevira, Inc., Germany). Samples were formed onto 18 gsm wet laid tissue.

TABLE 18

|  | Fluff Cellulose (gsm) | Bonding Fiber (gsm) | SAP Powder (gsm) | Latex Binder Resin (gsm) | Matrix Fiber (gsm) |
|---|---|---|---|---|---|
| Acquisition Layer | none | none | none | 6.0 | 34.0 |
| Distribution Layer | 30.3 | 3.5 | none | 1.3 | none |
| Storage Layer | 64.1 | 7 | 52.5 | 1.3 | none |

EXAMPLE 15

A second sample was produced which contained GenFlo 3060 styrene-butadiene copolymer as the latex bonder (GenCorp Specialty Polymers, Akron, Ohio).

EXAMPLE 16

A third sample was produced which contained GenFlo 9355 styrene-butadiene-acrylic terpolymer as the latex binder (GenCorp Specialty Polymers, Akron, Ohio). Two percent of Aerosol OT 75 obtained from Van Waters & Rodgers, Memphis, Tenn. a surfactant, was added to the aqueous latex bonder solution to render the acquisition layer hydrophilic.

The samples were tested for fluid acquisition rate and fluid retention testing of 0.9% saline solution according to the methods of Example 1 and 2 except that the amount of each fluid insult was 10 ml. The results are shown in Table 19.

TABLE 19

|  | Acquisition Rate (ml/sec) 10 ml saline insults | | | Fluid Retention (%) 10 ml saline insults | | | |
|---|---|---|---|---|---|---|---|
|  | 1st Insult | 2nd Insult | 3rd Insult | 1st Insult | 2nd Insult | 3rd Insult | Latex |
| Example 14 | 4.6 | 2.1 | 1.8 | 98.6 | 79.3 | 51.8 | AirFlex 192 |
| Example 15 | 5.6 | 3.3 | 2.3 | 98.8 | 79.8 | 50.3 | GenFlo 3060 |
| Example 16 | 7.1 | 2.5 | 4.0 | 99.0 | 79.8 | 50.3 | GenFlo 9355 |

Two additional variants were made of the third sample. The first variant contained 1% Aerosol OT surfactant, and the second variant had no surfactant added to the latex bonder emulsion. Samples (2.5 square inch) were placed on a horizontal surface. A 5 ml insult of 0.9% saline was poured onto each sample. The saline solution penetrated immediately into the samples having added surfactant. In samples without surfactant, the saline insult remained pooled on top of the sample for over an hour, at which time the test was terminated.

Examples 14–16 demonstrate that the wettability of an airlaid composite structure of the invention can be adjusted at the point of manufacture, and that even with large (6 denier) synthetic fibers, a minimal level of hydrophilicity must be present in the latex resin to achieve acceptable fluid penetration.

What is claimed is:

1. A fluid acquisition and distribution layer consisting essentially of
   (i) a porous top acquisition layer consisting essentially of latex-bonded synthetic matrix fibers having a length of from about 3 to about 15 mm, and, optionally, a surfactant, a pigment, an opacifier or a mixture thereof, and
   (ii) a bottom distribution layer in fluid communication with the top layer consisting of airlaid cellulose fibers, and a bonder selected from the group consisting of thermoplastic fibers, latex, and mixtures thereof; and, optionally, a surfactant, a pigment, an opacifier or a mixture thereof.

2. A fluid acquisition and distribution layer consisting essentially of
   (i) a porous top acquisition layer consisting essentially of latex-bonded synthetic matrix fibers having a length of from about 3 to about 15 mm, and, optionally, a surfactant, a pigment, an opacifier or a mixture thereof;
   (ia) optionally, a middle layer consisting essentially of fluff cellulose, or a blend of synthetic and cellulose fibers; and
   (ii) a bottom distribution layer in fluid communication with the top layer consisting of airlaid cellulose fibers, and a bonder selected from the group consisting of thermoplastic fibers, latex, and mixtures thereof; and, optionally, a surfactant, a pigment, an opacifier or a mixture thereof.

3. The acquisition and distribution layer of claim 2, wherein the length of the synthetic matrix fibers is from about 6 to about 12 mm.

4. The acquisition and distribution layer of claim 2, wherein the thickness of the synthetic matrix fibers is from about 3 to about 20 denier.

5. The acquisition and distribution layer of claim 4 wherein the thickness of synthetic matrix fibers is from about 6 to about 15 denier.

6. The acquisition and distribution layer of claim 2, wherein the synthetic matrix fibers is selected from the group consisting of polyethylene, polypropylene, polyethylene terephthalate, and mixtures thereof.

7. The acquisition and distribution layer of claim 2, wherein the latex is selected from the group consisting of an aqueous emulsion of ethylene vinyl acetate, acrylic, styrene-butadiene, or styrene-butadiene acrylic.

8. The acquisition and distribution layer of claim 2, wherein the cellulose fibers are selected from the group consisting of wood cellulose, cotton linter pulp, chemically modified cellulose, highly purified cellulose fibers, and mixtures thereof.

9. An absorbent structure, comprising
   (A) a fluid acquisition and distribution layer consisting essentially of
      (i) a porous top acquisition layer consisting essentially of latex-bonded synthetic matrix fibers having a length of from about 3 to about 15 mm, and, optionally, a surfactant, a pigment, an opacifier or a mixture thereof; and
      (ia) optionally, a middle layer consisting essentially of fluff cellulose, or a blend of synthetic and cellulose fibers; and
      (ii) a bottom distribution layer in fluid communication with the top layer consisting essentially of airlaid cellulose fibers, and a bonder selected from the group consisting of thermoplastic fibers, latex, and mixtures thereof, and, optionally, a surfactant, a pigment, an opacifier or a mixture thereof; and (B) a storage layer comprising cellulose fibers and super absorbent polymer particles wherein the fibers are thermally bonded, the storage layer in fluid communication with the distribution layer.

10. The structure of claim 9, wherein the length of the synthetic matrix fibers is from about 6 to about 12 mm.

11. The structure of claim 9, wherein the thickness of the synthetic matrix fibers is from about 3 to about 20 denier.

12. The structure of claim 11 wherein the thickness of the synthetic matrix fibers is from about 6 to about 15 denier.

13. The structure of claim 9, wherein the synthetic matrix fibers are selected from the group consisting of polyethylene, polypropylene, polyethylene terephthalate, and mixtures thereof.

14. The structure of claim 9, wherein the latex is selected from the group consisting of an aqueous emulsion of ethylene vinyl acetate, acrylic, styrene-butadiene, or styrene-butadiene acrylic.

15. The structure of claim 9, wherein the cellulose fibers of the liquid distribution layer and the liquid storage layer are the same or different and are selected from the group consisting of wood cellulose, cotton linter pulp, chemically modified cellulose, highly purified cellulose fibers, and mixtures thereof.

16. The structure of claim 9, wherein the super absorbent polymer particles are selected from the group consisting of polyacrylates, starch graft copolymers, cross-linked carboxymethylcellulose derivatives, hydrolyzed starch-acrylontrile graft co-polymers, saponified acrylic acid ester-vinyl co-polymers, modified cross-linked polyvinyl alcohols, neutralized cross-linked polyacrylic acids, cross-linked polyacrylate salts, and carboxylated cellulose.

17. The structure of claim 9, wherein the super absorbent polymer particles are surface cross-linked.

18. The structure of claim 9, wherein the acquisition layer has a basis weight range of about 20 to about 80 gsm.

19. The structure of claim 9, wherein the distribution layer has a basis weight range of about 20 to about 100 gsm.

20. The structure of claim 9, wherein storage layer has a basis weight range of about 60 to about 400 gsm.

21. An absorbent structure, comprising (i) an acquisition layer consisting essentially of latex-bonded PET matrix fibers having a length from about 3 to about 12 mm and a thickness from about 6 to 15 denier, wherein the acquisition layer has a basis weight range of about 20 to about 60 gsm;

(ii) a distribution layer consisting essentially of cellulose fibers which fibers are thermal-bonded or chemically modified, and wherein the distribution layer has a basis weight range of about 30 to about 90 gsm, the distribution layer in fluid communication with the acquisition layer; and (iii) a storage layer comprising cellulose fibers and super absorbent polymer particles wherein the fibers are thermally bonded, and wherein the storage layer has a basis weight range of about 70 to about 130 gsm, the storage layer in fluid communication with the distribution layer.

22. An absorbent structure, comprising (i) an acquisition layer consisting essentially of latex-bonded PET matrix fibers having a length from about 3 to about 12 mm and a thickness from about 6 to 15 denier, wherein the acquisition layer has a basis weight range of about 20 to about 60 gsm;

(ii) a distribution layer consisting essentially of cellulose fibers which fibers are thermal-bonded or chemically modified, and wherein the distribution layer has a basis weight range of about 30 to about 100 gsm, the distribution layer in fluid communication with the acquisition layer; and (iii) a storage layer comprising cellulose fibers and super absorbent polymer particles wherein the fibers are thermally bonded, and wherein storage layer has a basis weight range of about 250 to about 340 gsm, the storage layer in fluid communication with the distribution layer.

* * * * *